United States Patent
Le Floch et al.

(10) Patent No.: US 11,604,361 B2
(45) Date of Patent: Mar. 14, 2023

(54) OPTICAL DEVICE FOR FACILITATING READING

(71) Applicants: UNIVERSITÉ DE RENNES 1, Rennes (FR); Albert Le Floch, Rennes (FR)

(72) Inventors: Albert Le Floch, Rennes (FR); Guy Ropars, Rennes (FR)

(73) Assignees: Albert Le Floch, Rennes (FR); UNIVERSITÉ DE RENNES 1, Rennes (FR)

( * ) Notice: Subject to any disclaimer, the term of this patent is extended or adjusted under 35 U.S.C. 154(b) by 144 days.

(21) Appl. No.: 16/765,278

(22) PCT Filed: Aug. 3, 2018

(86) PCT No.: PCT/FR2018/052011
§ 371 (c)(1),
(2) Date: May 19, 2020

(87) PCT Pub. No.: WO2019/106243
PCT Pub. Date: Jun. 6, 2019

(65) Prior Publication Data
US 2020/0310141 A1    Oct. 1, 2020

(30) Foreign Application Priority Data
Nov. 30, 2017 (FR) ...................................... 1701260

(51) Int. Cl.
*G02B 27/02* (2006.01)
*G02C 7/10* (2006.01)
*G02C 7/12* (2006.01)

(52) U.S. Cl.
CPC ........... *G02B 27/021* (2013.01); *G02C 7/101* (2013.01); *G02C 7/12* (2013.01)

(58) Field of Classification Search
CPC ......... G02B 27/021; G02C 7/101; G02C 7/12
USPC .......................................................... 351/49
See application file for complete search history.

(56) References Cited

U.S. PATENT DOCUMENTS

| | | | |
|---|---|---|---|
| 6,181,300 B1 | 1/2001 | Poon | |
| 2012/0019639 A1 | 1/2012 | Chang | |
| 2013/0017520 A1* | 1/2013 | Yoo ...................... | H04R 25/606 434/247 |

(Continued)

FOREIGN PATENT DOCUMENTS

| | | |
|---|---|---|
| FR | 2969893 A1 | 6/2012 |
| FR | 2979464 A1 | 1/2013 |

OTHER PUBLICATIONS

International Search Report for corresponding application PCT/FR2018/052011 filed Aug. 3, 2018; dated Dec. 10, 2018.

*Primary Examiner* — Joseph P Martinez
*Assistant Examiner* — Mitchell T Oestreich
(74) *Attorney, Agent, or Firm* — Cantor Colburn LLP

(57) ABSTRACT

The invention relates to an optical device (FILT) for filtering light received, by polarisation or mechanically, from a medium presenting a graphic and/or textual content, characterized in that cycles of opening and closing a vision space, in a visible light spectrum, are realized periodically using the optical device (FILT) at a preset frequency Fd and in that the successive open periods each have a duration (T1) comprised in an interval of values ranging from 15 to 35% of the duration (T) of the realized cycles.

14 Claims, 1 Drawing Sheet

(56) References Cited

U.S. PATENT DOCUMENTS

2013/0169603 A1* 7/2013 Bae .................. H04N 13/398
  345/204
2014/0336723 A1 11/2014 Ben-Ezra

* cited by examiner

OPTICAL DEVICE FOR FACILITATING READING

1. TECHNICAL FIELD

The present disclosure relates to an optical device. The disclosure relates more particularly to an optical filtering device facilitating the reading of content, in particular text content, for people prone to dyslexia.

2. BACKGROUND

Dyslexia is commonly defined as a set of reading disorders that appear in childhood. They are specific learning disabilities whose causes appear complex and have been and still are the subject of numerous studies in various fields.

It is generally excluded to consider that the causes of dyslexia can be only of sensory, social or psychological order.

Studies in the field of neuroscience suggest that it could be a specific neurological disorder.

Advances in medical imagery have highlighted the role of some areas of the brain in reading and language skills.

The solutions provided to treat dyslexia disorders are based on fun work and activities depending on the difficulties specific to each subject. The objective of such support is to provide the subject with disorders with reading autonomy. The known methods are developed around work in fields such as psychology, psychomotricity and orthoptics, for example.

Recently, studies have been conducted, establishing a correlation between features specific to the mechanism of vision and the presence of specific dyslexia disorders. The publication "Left-right asymmetry of the Maxwell spot centroids in adults without and with dyslexia (Le Floch A, Ropars G. 2017, Proc. R. Soc. B 284: 20171380, http://dx.doi.org/10.1098/rspb.2017.1380) mentions the role of the foveas, located in the human eye, in the construction of perceived images, at the brain, and the fact that identical or substantially identical features for each eye of the same subject lead to dysfunctions in the process of vision and phonological processing at the brain. The transmission of a mirror image from one hemisphere to another, for example, substantially disrupts the process of reading graphic elements or text content in subjects with disorders characterising dyslexia. Disorders related to fixation instability and/or posturological instability, or else binocular convergence defects related to the oculomotor muscles, can also cause visual clutter such as the mirror effect.

3. BRIEF SUMMARY

The disclosure allows improving at least some of the disadvantages of the prior art by proposing an optical filtering device adapted to facilitate the reading of content, such as graphic content, on all types of media, and in particular on a paper or on a screen. The proposed device operates successive opening and closing periods of a viewing space or plane, at least in the visible light spectrum. The light received via the viewing space or plane is thus transmitted or inhibited (or even eliminated) periodically, by an obstacle (polarising filter) implemented by the optical device, according to successive cycles operated at a predetermined frequency. The successive opening periods of the viewing space each have a duration comprised within an interval of values ranging from 15 to 35% of the total duration of the operated cycles.

The optical device according to the disclosure comprises a control unit and one or more (for example two) filtering modules each adapted to periodically obscure (inhibit) light (by closing the viewing space) in a visible light spectrum. The optical device is configured for the periodic opening and closing (or inhibition) of a viewing space traversed by light, in a visible light spectrum, according to successive cycles operated at a predetermined frequency Fd. Each cycle has a duration T and comprises a viewing space opening period of a duration T1 followed or preceded by a viewing space closing period of a duration T2. The device is configured so that the duration T1 of the viewing space opening periods is comprised within an interval of values ranging from 15 to 35% of the duration T of the cycles.

According to an embodiment of the disclosure, the predetermined frequency Fd is defined by a user of the optical filtering device.

Such a device takes, for example, the form of eyeglasses frame comprising, instead of the usual corrective lenses, one or more filter elements comprising controllable liquid crystals useful for controlling the polarisation of the light applied thereto. The device comprises, for example, a miniaturized control unit, embedded in the frame, and adapted for controlling the orientation of the liquid crystals. This polarisation is variable over time, under the control of the aforementioned control unit.

According to a variant, the optical filtering device takes the form of a filtering plane adapted to be positioned on or in front of a screen of a graphic rendering device.

Advantageously, the frequency Fd of the cycles (for example of polarisation of the received light) thus operated is comprised within an interval of values ranging from 60 to 90 Hz, thanks to a tunable system then operating as a visual anti-congestion device. This system takes advantage of the Hebbian mechanisms in the neurons of the cortex.

According to one embodiment of the disclosure, the predetermined opening and closing frequency of the viewing space is selected discretely, that is to say from a plurality of predetermined frequencies in the frequency interval mentioned above.

According to one embodiment, the frequency Fd varies over time, in order to further facilitate, in some cases, the erasure of the visual clutter and the binocular stability According to one embodiment, the frequency Fd varies by increasing in successive steps up to a maximum value in a first rate, called increasing rate, then varies by decreasing in successive steps to a minimum value in a second rate, called decreasing rate, the increasing and decreasing variations repeating iteratively over time.

According to one embodiment, said decreasing rate is equal to said increasing rate.

According to one embodiment, said successive steps are of equal duration.

According to one embodiment, said successive steps vary in duration so that the value of said frequency Fd changes in a triangle, saw, or sinusoidal waveform between said maximum value and said minimum value.

According to one embodiment of the disclosure, the duration T1 of the opening periods of the viewing space varies over time.

According to one embodiment of the disclosure, the filtering module comprises polarising elements and elements of the liquid crystal type adapted for polarising the light received, transmitted via a viewing space.

According to one embodiment of the disclosure, the closure of the viewing space performed in a visible light spectrum is performed by the orientation of liquid crystals assembled in one or more surfaces (or one or more planes) in the optical device according to the disclosure.

The term "viewing space" is to be interpreted here as all or part of the field of vision of a human subject. It can be the field of vision of one eye taken in isolation, or a combination of the field of vision of both eyes, or a subset of either one of these variants. The term "viewing plane" then means a section of the viewing space as previously defined by a plane perpendicular to the mean direction of the light transmitted via the viewing space, from an observed medium and to an eye or to the eyes of a subject.

Thus, the "viewing space" can be defined as a portion of space comprised between the eyes of a human subject and an object viewable by this subject, by either one of his eyes, or both. A "viewing plane" is to be interpreted here as a plane defining a section of this space.

Thus the terms "opening a viewing space" or "opening a viewing plane" are to be interpreted here as a normal transmission (not deliberately altered or inhibited by a device) of the visible light, transmitted via the viewing space. Conversely, the terms "closing a viewing space" or "closing a viewing plane" should be interpreted here as establishing and maintaining a barrier (a filter or an obstacle), more or less opaque, to the transmission of visible light, via the viewing space, for a predetermined duration. An alternation of opening and closing (inhibition or attenuation of the received light) operations of the same viewing space thus constitutes a "filtering" operation within the meaning of the present description. The term "opening a viewing space" can therefore be interpreted as a total absence of filtering and the term "opening a viewing space" can therefore be interpreted as at least a partial presence of filtering.

Advantageously, the use of a range of frequencies of the opening and closing cycles of the viewing space, from 60 Hz, allows dispensing with the known effects of blinking (or flickering) perceptible by the eye of the human being, the limit of perception of blinking by the eye being around 60 Hz, for the human being (excluding consideration of animal species).

Advantageously, the alternation of opening and closing periods of the viewing space in the visible light spectrum, oriented towards a medium, allows a "focusing" of the brain of a subject looking at this medium, on an image representative of the content represented on the observed medium, then, a disappearance of this same image from the subject's view before it is transmitted in the form of a mirror image between a cerebral hemisphere and the other cerebral hemisphere of this subject looking at this medium. The delay required for the brain to transmit an image, perceived by the eye, between one hemisphere and the other hemisphere, in the form of a mirror image for the latter, is of the order of 10 ms.

Thus, the brain favours the transmitted image, from the observed medium, relative to its mirror image, and the existing confusion in the subject, which has a strong similarity in the features of his two foveas, is less or significantly reduced for reading the (graphic and/or text) content shown on the medium, through the optical filtering device, in particular when this content is representative of one or more text content.

Advantageously, the use of a switch configured to selectively obtain a permanent opening of the viewing space ("ordinary" vision without filtering) and an opening of the viewing space as described above (alternating opening and closing periods of the viewing space) allows a user subject to dyslexic disorders to compare his usual performance in reading (corresponding to an ordinary vision) with his performance obtained under electronic control of the filtering of the viewing space according to the disclosure (alternating opening and closing periods of the viewing space) after optional optimisation of his own parameters (frequency and cyclic ratio parameters allowing the user to obtain better reading comfort).

Advantageously, the optical filtering device according to the disclosure is functional with natural light or polarised light. According to one embodiment of the disclosure, the filtering device simultaneously operates a filtering in the viewing space or the viewing plane in an identical or similar manner for the two eyes of a subject using it.

The disclosure also relates to an optical filtering method in an optical device, the device comprising a control unit and an optical filtering module adapted for opening and closing a viewing space in a visible light spectrum, the method comprising periodic openings and closings of a viewing space by successive cycles operated at a predetermined frequency, each cycle having a duration T and comprising a viewing space opening period of duration T1 followed or preceded by a viewing space closing period of duration T2, wherein the duration T1 of the viewing space opening periods is comprised within an interval of values ranging from 15 to 35% of the duration T of the cycles.

4. BRIEF DESCRIPTION OF THE DRAWINGS

The disclosure will be better understood, and other features and advantages will appear upon reading the description which follows, the description making reference to the appended drawings among which:

5. DETAILED DESCRIPTION

Figure 2:
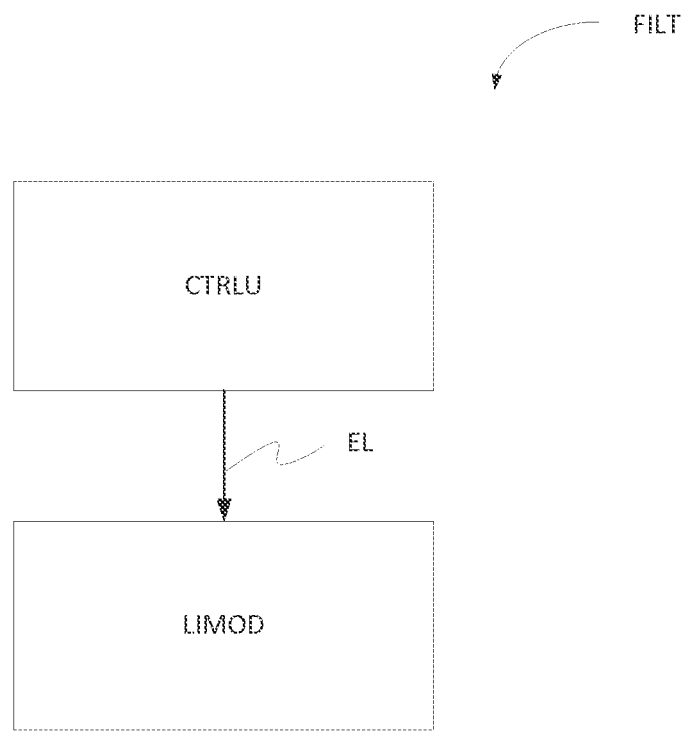
FIG. 2 is a structural representation of the architecture of an optical device FILT according to a particular and non-limiting embodiment of the disclosure.

In FIG. 2, the modules represented are functional units, which may or may not correspond to physically distinguishable units. For example, these modules or some of them are grouped into a single component. Conversely, according to other embodiments, some modules are composed of separate physical entities.

Figure 1:
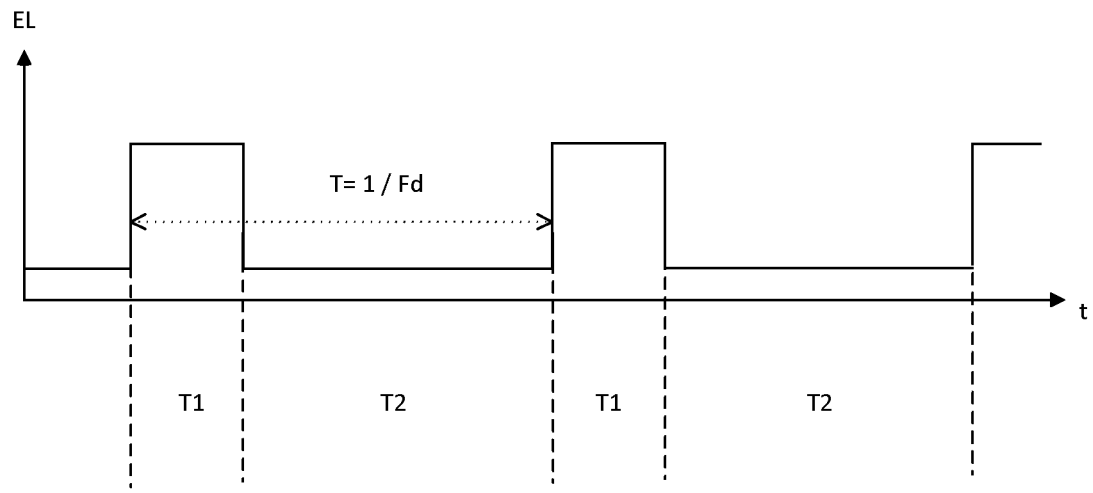
FIG. 1 is a diagram of a signal EL for commanding (controlling) an optical filtering module LIMOD according to a particular and non-limiting embodiment of the disclosure.

FIG. 1 is a temporal representation of a signal EL for controlling the opening and closing of a viewing space or plane in the visible light spectrum, in an optical filtering device FILT, according to a particular and non-limiting embodiment of the disclosure. The signal EL varies according to the time t and periodically takes two successive states. According to the preferred embodiment, an assertion of the signal EL in the high state controls an opening of the viewing space through the optical device FILT capable of transmitting visible light, in a generally discontinuous manner, of a graphic and/or text content from any medium, such as a book or a screen, for example.

According to similar reasoning, the signal EL controls the closing (shutter or inhibition) of the viewing space when it is positioned in the low state. The signal EL is a periodic signal of predetermined frequency Fd such that Fd=1/(T1+T2). T1 is the opening period of the viewing space or plane, in the visible light spectrum, namely a transmission period of the light received from a medium carrying a pattern representing a graphic and/or text content towards which the viewing space is oriented. T2 is the period, called closing period of the viewing space, during which the viewing space is shuttered (closed) or the transmission of visible light is interrupted or inhibited, or in other words the period during which the graphic and/or text content present on a medium towards which the viewing space is oriented is no longer normally perceptible by the eye(s) by performing a visualisation or a reading. The term "graphic content" should be interpreted here as any content represented on any medium, in particular in paper format but not only, and consisting of elementary elements such as, for example juxtaposed dots or pixels, so that the content represents elements of various forms and in particular one or more text contents constructed from signs or symbols from one or more alphabets.

Thus, a text content affixed to a medium here corresponds to content interpretable in one or more languages, capable of being read and interpreted by a subject, user of the optical filtering device, positioned so that a subject can watch the medium (book or screen, for example) for a reading or viewing operation. Such an optical filtering device is, for example, a pair of eyeglasses, a helmet, a mask, an intermediate screen, a filtering plane configured to be disposed in front or against a rendering screen. This list of examples is not exhaustive.

According to one embodiment of the disclosure, the cyclic ratio T1/(T1+T2) between the opening and closing (or inhibition) periods of the viewing space, of duration T1 and T2 respectively, has a value comprised between 15% and 35% of the cycle, and the variation frequency Fd of the signal EL is comprised between 60 Hz and 90 Hz.

Preferably, the cyclic ratio T1/(T1+T2) between the opening and closing (or inhibition) periods of the viewing space, respectively of duration T1 and T2, has a value comprised between 22% and 32% of the cycle, and the variation frequency Fd of the signal EL is comprised between 70 Hz and 85 Hz.

More preferably, the signal frequency is equal to 70 Hz or 84 Hz and the cyclic ratio T1/(T1+T2) is equal to 20%.

Advantageously, the control signal EL can be easily sustainedly forced in its state associated with an activation of the light beam, which corresponds to a disengagement of the optical filtering method implemented in the device FILT according to the disclosure. It would thus be possible not to implement the optical filtering method, in a filtering device according to the disclosure, in the case where, for a non-dyslexic subject, visual discomfort would appear due to the discontinuity of opening the viewing space, and without then having to successively remove/affix in the viewing space, the device.

Advantageously, it is possible to refine the adjustment of the frequency Fd in the interval of values described in order to adapt the period T to the sensitivity of a user of the optical filtering device FILT, in the indicated frequency range. Indeed, each individual has his own sensitivity in terms of vision and perceives more or less variations in the frequency of a light beam. Thus, a fine adjustment can be made accessible to the user by means of an adjustment button, a cursor, implemented physically or via any user interface (graphic elements of a menu on a control screen, for example, or on a remote control device).

FIG. 2 is a structural representation of the optical filter device FILT according to a particular and non-limiting embodiment of the disclosure. This figure represents the overall architecture of the optical device FILT, also commonly known as "eyeglasses" or "helmet". The optical device FILT comprises two main modules which are a control unit CTRLU and a filtering module LIMOD.

The control unit CTRLU is the core of the system in terms of control and comprises a conventional bistable (or chopper) circuit, adapted for generating the signal EL. The bistable chopping circuit of the control unit CTRLU delivers the signal EL characterised by the frequency Fd and by its cyclic ratio T1/(T1+T2). Obviously the control unit CTRLU comprises all the usual elements implemented in such an architecture, such as, for example, one or more operational amplifiers, resistors and capacitors, one or more diodes, a power supply (possibly on battery/batteries), a reset circuit, a power supply supervision circuit, a power interface, a current amplifier, the list of these elements is not exhaustive. The architectural details of the control unit CTRLU are not further described since they are not useful for understanding the disclosure. According to an embodiment of the disclosure, the module CTRLU comprises a bistable circuit built around an operational amplifier, coupled to a current amplification circuit. The optical filtering module LIMOD is a module comprising one or more surfaces comprising polarised liquid crystals, the polarisation of which is electrically commanded by an electrical signal. The module LIMOD is then adapted for filtering light transmitted in the visible light spectrum, or substantially wider. Advantageously, the viewing space can be more or less filtered to be then configured for the optimised reading of a more or less large surface. Such focusing can be achieved by the use of additional optical elements (lenses) or else mechanical elements (diaphragms, for example), or both at the same time. Thus, the filtering module is for example implemented in the form of eyeglasses frames comprising one or more translucent surfaces, instead of the corrective glasses of corrective eyeglasses, which surfaces carry elements of the liquid crystal type which can be oriented by polarisation. For example, a support surface can be configured to comprise glazing between which a nematic liquid crystal is sandwiched in the form of droplets immobilised in a polymer between two glass surfaces covered with a thin metallic layer to constitute a capacitor. The filtering module thus produced switches for example from a slightly opaque state when powered to a translucent state in the absence of power.

Liquid crystals, due to their variable chemical structures, can behave like dipoles capable of being oriented along field lines, under the action of an electric field.

As a result, the optical filtering module LIMOD can operate a variation in the directivity of light transmitted into the viewing space by creating a phenomenon of directivity of light rays from a medium viewed by a subject. The implementation details of the liquid crystal filter elements (polarising elements) are not further described here, since they are well known to the person skilled in the art and are not useful for the understanding of the disclosure.

The terms "closure", "shutter", or else "inhibition" of the light transmitted in the described viewing space, which is oriented between a medium viewed or read and the eyes of a subject, should be interpreted here as corresponding to a partial or total attenuation of the amplitude of transmitted light, due to the optical filtering operated by the induced mechanism of directivity of the light perceived by the subject, thanks to the polarisation performed by the optical filtering module LIMOD.

Advantageously, the optical filtering device FILT operates a vertical or substantially vertical polarisation of the received light, transmitted from a medium viewed or read. Thus, when this medium is a screen or any rendering device (of display type) itself polarised at +45°, 0°, or −45° relative to the vertical, which is frequently the case for rendering equipment of visual content (TV, computer, smartphone, for example), a transmission of light between the visualised medium and the eyes of a subject observing this medium is always possible. In contrast, and according to a similar reasoning, if the optical filtering device FILT comprised a module LIMOD polarising the light received with a polarisation axis at +45° and used for reading content on a rendering device (screen, display) polarising the light emitted with a polarisation axis of −45°, there would be a total or almost total shutter of the light transmitted in the viewing space, even in the open position of the device FILT.

It is the ability to successively open and close the viewing space between a visualised reading medium and a subject operating the reading, which medium presents one or more graphic and/or text contents, under the control of the bistable module of the unit CTRLU, which advantageously allows the brain of a subject to favour an image rather than its mirror image, perceived from the medium when the latter is observed via the optical filtering device FILT according to the disclosure. Advantageously, this allows to consequently help reading and deciphering text contents, in a subject having dyslexic disorders.

Advantageously, the control unit CTRLU comprises as output a signal EL for opening (or closing/shuttering/inhibiting) the viewing space, connected at the input of the optical filtering module LIMOD.

In other words, the variations of the control signal EL of the optical filtering device LIMOD, operated by the control unit CTRLU comprising a bistable circuit, at a predetermined frequency Fd, allow acting on the filtering of the light received from a medium carrying graphic content. Thus, this graphic content is successively then less (or no longer) visible by a subject observing it, according to successive cycles of total length T operated at the predetermined frequency Fd, which allows increasing the readability of the content observed for a subject having dyslexic disorders. According to the disclosure, the successive opening periods T1 of the viewing space each have a duration comprised within an interval of values ranging from 15 to 35% of the duration T of the cycles.

The frequency Fd of the cycles (each comprising an opening period of the viewing space and a closing period of the viewing space) is comprised between 60 and 90 Hz.

According to one embodiment, the frequency Fd is fixed.

According to another embodiment, the frequency Fd varies over time.

According to a particular embodiment, the frequency Fd varies by increasing in successive steps up to a maximum value in a first rate, called the increasing rate, then varies by decreasing by successive steps to a minimum value in a second rate, called decreasing rate, the increasing and decreasing variations repeating iteratively over time.

According to a particular embodiment, the decreasing rate is equal to the increasing rate.

According to a particular embodiment, the successive steps are of equal duration.

According to another particular embodiment, the successive steps vary in duration so that the value of said frequency Fd changes in a triangle, saw, or sinusoidal waveform between said maximum value and said minimum value.

Advantageously, the duration T1 of the activation periods varies over time, evolving continuously or discontinuously between limit values ranging from 15 to 35% of the duration T of the cycles. Here "continuously" means an evolution by increment of the successive steps of equal durations.

The wobulation phenomenon thus created and applied to the predetermined frequency Fd (variation of the frequency Fd) allows scanning a large number of frequencies between 60 Hz and 90 Hz, some of which will be more effective for reading assistance. These more effective frequencies vary depending on the dyslexic subject. By scanning all frequencies between 60 and 90 Hz, the device of the disclosure requires no prior adjustment and becomes effective for a large number of users.

The same advantage arises from variations in the duration T1 of the opening periods of the viewing space.

This wobulation phenomenon thus allows and in some cases, to reduce even more the troubles related to dyslexic disorders.

The disclosure is not limited to the sole embodiments described above, but applies to any optical device for filtering the received light, adapted for the observation of a graphic and/or text content on any medium (screen or book, for example), implementing successive operations of opening a viewing space and closing this same viewing space, periodically, according to successive cycles operated at a predetermined frequency Fd between 60 Hz and 90 Hz such that the successive opening periods T1 each have a duration comprised within an interval of values ranging from 15 to 35% of the duration T of the operated cycles. For example and according to a variant, the opening and closing of the viewing space or of the viewing plane can be performed by implementing one or more mechanical elements controlled according to the described method (frequency Fd and cyclic ratio T1).

The invention claimed is:

1. An optical device (FILT) comprising:
   a control unit (CTRLU) and
   a filtering module (LIMOD) adapted for opening and closing a viewing space in a visible light spectrum,
   wherein said optical device (FILT) is configured to periodically open and close said viewing space according to successive cycles operated at a frequency Fd, each cycle having a duration T and comprising a viewing space opening period of duration T1 followed or preceded by a viewing space closing period of duration T2,
   wherein said frequency Fd is comprised within an interval of values ranging from 60 to 90 Hz and the duration T1 of the viewing space opening periods is comprised within an interval of values ranging from 15 to 35% of the duration T of the cycles;
   wherein said cycles reduce mirror images perceived by dyslexic subjects during reading.

2. The optical device (FILT) according to claim 1, wherein said frequency Fd is comprised within an interval of values ranging from 70 to 85 Hz.

3. The optical device according to claim 1, wherein the frequency Fd varies over time.

4. The optical device according to claim 3, wherein the frequency Fd varies by increasing in successive steps up to a maximum value in a first rate, called increasing rate, then varies by decreasing in successive steps to a minimum value in a second rate, called decreasing rate, the increasing and decreasing variations repeating iteratively over time.

5. The optical device according to claim 4 wherein said decreasing rate is equal to said increasing rate.

6. The optical device according to claim 5, wherein said successive steps are of equal duration.

7. The optical device according to claim 5, wherein said successive steps vary in duration so that the value of said frequency Fd changes in a triangle, saw, or sinusoidal waveform between said maximum value and said minimum value.

8. The optical device according to claim 1, wherein the duration T1 of said opening periods of the viewing space varies over time.

9. The optical device (FILT) according to claim 1, wherein said filtering module (LIMOD) comprises polarizing elements and elements of the liquid crystal type adapted for polarizing the light received, transmitted via said viewing space.

10. The optical device (FILT) according to claim 9, wherein said polarization of the light received via said viewing space is a vertical polarization.

11. The device according to claim 1, wherein it is of a type comprised in the list: a pair of eyeglasses, a helmet, a mask, an intermediate screen, a filtering plane configured to be disposed in front or against a rendering screen.

12. The device according to claim 1, wherein said predetermined frequency is defined by a user of said device.

13. An optical filtering method for facilitating reading of graphic and/or text content on any medium by dyslexic subjects, said method being implemented in an optical device (FILT) comprising a control unit (CTRLU) and a filtering module (LIMOD) adapted for opening and closing a viewing space in a visible light spectrum, said method comprising
periodic openings and closings of a viewing space by successive cycles operated at a predetermined frequency Fd, each cycle having a duration T and comprising a viewing space opening period of duration T1 followed or preceded by a viewing space closing period of duration T2,
wherein said frequency Fd is comprised within an interval of values ranging from 60 to 90 Hz and in that the duration T1 of the viewing space opening periods is comprised within an interval of values ranging from 15 to 35% of the duration T of the cycles;
wherein said cycles reduce mirror images perceived by said dyslexic subjects during reading.

14. The optical filtering method according to claim 13, according to which said frequency Fd is comprised within an interval of values ranging from 70 to 85 Hz.

* * * * *